(12) United States Patent  
Morman et al.

(10) Patent No.: US 7,591,810 B2  
(45) Date of Patent: Sep. 22, 2009

(54) ABSORBENT GARMENT HAVING A BODY CONFORMING ABSORBENT COMPOSITE

(75) Inventors: Michael T. Morman, Alpharetta, GA (US); James M. Carr, Kaukauna, WI (US); Yung H. Huang, Appleton, WI (US); Eric D. Johnson, Larsen, WI (US); Jennifer L. Marvin, Greenville, WI (US); Mary Jo Meyer, Neenah, WI (US); Thomas H. Roessler, Appleton, WI (US); Paul T. Van Gompel, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1365 days.

(21) Appl. No.: 10/325,456

(22) Filed: Dec. 19, 2002

(65) Prior Publication Data

US 2004/0122412 A1    Jun. 24, 2004

(51) Int. Cl.  
*A61F 13/15* (2006.01)

(52) U.S. Cl. .............. 604/385.24; 604/385.27; 604/385.16; 604/385.29; 604/385.01; 604/393; 604/386

(58) Field of Classification Search .......... 604/358–402  
See application file for complete search history.

(56) References Cited

U.S. PATENT DOCUMENTS

| | | | |
|---|---|---|---|
| 1,931,357 A | 10/1933 | Potwin | |
| 2,122,417 A | 7/1938 | Fridolph | |
| 2,252,019 A | 8/1941 | Meinecke et al. | |
| 2,252,992 A | 8/1941 | Steiner | |
| 2,481,351 A | 9/1949 | Rosenfield | |
| 3,050,063 A | 8/1962 | Margraf | |
| 3,828,785 A | 8/1974 | Gamm et al. | |

(Continued)

FOREIGN PATENT DOCUMENTS

CA    2255465    6/2000

(Continued)

OTHER PUBLICATIONS

International Search Report in corresponding International Application No. PCT/US03/27992, dated Jan. 16, 2004, 7 pages.

*Primary Examiner*—Jacqueline F. Stephens  
(74) *Attorney, Agent, or Firm*—H. Michael Kubicki (57) ABSTRACT

An absorbent garment includes a front body panel having a terminal waist edge and a terminal crotch edge and a rear body panel having a terminal waist edge and a terminal crotch edge. The terminal crotch edge of the rear body panel is longitudinally spaced from and forms a gap with the terminal crotch edge of the front body panel. An absorbent composite bridges the gap between the front and rear body panels with first and second terminal edges overlying and connected to the front and rear body panels respectively. In one embodiment, the terminal edges of the absorbent composite are the only portion of the absorbent composite connected to the front and rear body panels. In another embodiment, the absorbent composite is further connected to the front and rear body panels at first and second attachment locations proximate a longitudinally extending centerline of the absorbent composite and longitudinally spaced from the first and second terminal edges. Methods of using the absorbent garments are also provided.

23 Claims, 5 Drawing Sheets

U.S. PATENT DOCUMENTS

| | | | |
|---|---|---|---|
| 4,022,210 A | | 5/1977 | Glassman |
| 4,022,212 A | * | 5/1977 | Lovison .................... 604/395 |
| 4,280,230 A | * | 7/1981 | LaFleur ........................ 2/408 |
| 4,425,130 A | | 1/1984 | DesMarais |
| 4,496,360 A | | 1/1985 | Joffe et al. |
| 4,671,793 A | | 6/1987 | Hults et al. |
| 4,695,279 A | | 9/1987 | Steer |
| 4,747,846 A | * | 5/1988 | Boland et al. .......... 604/385.22 |
| 4,808,176 A | | 2/1989 | Kielpikowski |
| 4,834,736 A | | 5/1989 | Boland et al. |
| 4,961,736 A | | 10/1990 | McCloud |
| 4,964,860 A | | 10/1990 | Gipson et al. |
| 5,019,068 A | | 5/1991 | Perez et al. |
| 5,185,011 A | | 2/1993 | Strasser |
| 5,217,447 A | | 6/1993 | Gagnon |
| 5,221,277 A | | 6/1993 | Beplate |
| 5,370,632 A | | 12/1994 | Beplate |
| 5,389,095 A | | 2/1995 | Suzuki et al. |
| 5,403,303 A | | 4/1995 | Beplate |
| 5,405,342 A | | 4/1995 | Roessler et al. |
| 5,409,476 A | | 4/1995 | Coates |
| 5,435,014 A | | 7/1995 | Moretz et al. |
| 5,549,593 A | * | 8/1996 | Ygge et al. ................. 604/391 |
| 5,562,648 A | | 10/1996 | Peterson |
| 5,593,400 A | | 1/1997 | O'Leary |
| 5,690,627 A | | 11/1997 | Clear et al. |
| 5,707,364 A | | 1/1998 | Coates |
| 5,814,037 A | | 9/1998 | Coates |
| 5,846,232 A | | 12/1998 | Serbiak et al. |
| 5,853,405 A | | 12/1998 | Suprise |
| 5,891,122 A | | 4/1999 | Coates |
| 5,891,124 A | | 4/1999 | Nomura et al. |
| 6,010,586 A | | 1/2000 | Suprise |
| 6,142,983 A | | 11/2000 | Suprise et al. |
| 6,168,585 B1 | | 1/2001 | Cesco-Cancian |
| 6,169,225 B1 | | 1/2001 | Otsubo |
| 6,174,303 B1 | | 1/2001 | Suprise et al. |
| 6,217,563 B1 | | 4/2001 | Van Gompel et al. |
| 6,254,583 B1 | | 7/2001 | Coates |
| 6,336,923 B1 | | 1/2002 | Fujioka et al. |
| 6,375,646 B1 | | 4/2002 | Widlund et al. |
| 6,423,045 B1 | | 7/2002 | Wise et al. |
| 6,458,110 B1 | | 10/2002 | Lavon et al. |
| 6,478,786 B1 | | 11/2002 | Glaug et al. |
| 6,478,787 B1 | * | 11/2002 | Ihrfelt et al. ............. 604/385.3 |
| 6,514,233 B1 | * | 2/2003 | Glaug .................... 604/385.25 |
| 6,547,774 B2 | * | 4/2003 | Ono et al. ............. 604/385.29 |
| 6,755,808 B2 | * | 6/2004 | Balogh et al. .......... 604/385.28 |
| 2001/0016720 A1 | * | 8/2001 | Otsubo .................... 604/385.22 |
| 2002/0007162 A1 | * | 1/2002 | Cammarota et al. ......... 604/361 |
| 2002/0112982 A1 | * | 8/2002 | Stagray et al. ............... 206/494 |
| 2002/0138065 A1 | * | 9/2002 | Yeater et al. ................. 604/395 |
| 2002/0143311 A1 | * | 10/2002 | Brisebois ............... 604/385.01 |
| 2002/0147439 A1 | * | 10/2002 | Tanaka et al. ............... 604/398 |
| 2002/0151864 A1 | * | 10/2002 | Otsubo et al. .......... 604/385.29 |
| 2002/0161348 A1 | | 10/2002 | Mishima et al. |
| 2002/0169432 A1 | * | 11/2002 | Fell et al. ................ 604/385.14 |
| 2005/0004549 A1 | * | 1/2005 | Maas et al. ............. 604/385.29 |

FOREIGN PATENT DOCUMENTS

| | | |
|---|---|---|
| EP | 0 374 542 B1 | 11/1994 |
| EP | 0 763 353 A2 | 3/1997 |
| EP | 0 585 766 B1 | 4/1998 |
| EP | 1 034 760 A | 9/2000 |
| EP | 1 064 895 A | 1/2001 |
| EP | 0 648 482 B1 | 3/2001 |
| EP | 1 101 469 A2 | 5/2001 |
| EP | 1 132 067 A2 | 9/2001 |
| EP | 1 177 782 A | 2/2002 |
| GB | 2 253 131 A | 9/1992 |
| JP | 6125936 A2 | 10/1992 |
| JP | 8280726 A2 | 4/1995 |
| WO | WO 91/08725 | 6/1991 |
| WO | WO 9820824 A1 * | 5/1998 |
| WO | WO 99/63921 | 12/1999 |

* cited by examiner

ABSORBENT GARMENT HAVING A BODY CONFORMING ABSORBENT COMPOSITE

BACKGROUND

The present invention relates generally to an absorbent garment, and in particular, to an absorbent garment having a body conforming absorbent composite.

Absorbent garments, and in particular disposable absorbent garments, often include an absorbent composite and one or more body panels connected to the absorbent composite. Typically, the absorbent composites are secured to the body panels along the peripheral side edges of the absorbent composite. As such, the absorbent composite can reduce or otherwise affect the extensibility of the body panel, especially when it is desired to have a wider absorbent composite. In addition, the absorbent composite typically is not able to conform to the body of the user independently of the body panels, and can therefore distort the panels when fitted to a user or can be resistant to bunching in the crotch region thereby causing potential discomfort to the user.

SUMMARY

Briefly stated, in one embodiment, an absorbent garment includes a front body panel having a terminal waist edge and a terminal crotch edge and a rear body panel having a terminal waist edge and a terminal crotch edge. The terminal crotch edge of the rear body panel is longitudinally spaced from and forms a gap with the terminal crotch edge of the front body panel. An absorbent composite includes a first and second longitudinally spaced terminal edge and opposite laterally spaced side edges. The absorbent composite bridges the gap between the front and rear body panels with the first and second terminal edges overlying and connected to the front and rear body panels respectively. The terminal edges of the absorbent composite are the only portion of the absorbent composite connected to the front and rear body panels.

In another embodiment, the absorbent composite bridges the gap between the front and rear body panels with the first and second terminal edges overlying and connected to the front and rear body panels respectively. In addition, the absorbent composite is connected to the front and rear body panels at first and second attachment locations proximate a longitudinally extending centerline of the absorbent composite and longitudinally spaced from the first and second terminal edges. The absorbent composite has a first and second unattached region defined between the first and second attachment locations and the first and second terminal edges respectively.

In another aspect, methods of using the absorbent garments include applying the absorbent garment to the body of a user having legs, applying a force to the opposite side edges of the absorbent composite with the legs of the user and thereby laterally gathering the absorbent composite between the opposite side edges thereof in at least the portion of the absorbent composite bridging the gap between the front and rear body panels. In another aspect, methods of instructing the user about the use of the garment are also provided.

The present embodiments provide significant advantages over other absorbent garments and methods for the use thereof. For example, the connection between the absorbent composite and the body panels allows the absorbent composite to bunch or gather in the crotch region as the garment is worn by or applied to the user, thereby increasing the comfort of the user. In addition, the width of the absorbent composite can be varied, and made relatively wide, since it is permitted to bunch or gather in the crotch region. In this way, the absorbent capacity of the garment can be increased without affecting the comfort or fit of the garment.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

Many of the features and dimensions portrayed in the drawings, and in particular the presentation of layer thicknesses and the like, have been somewhat exaggerated for the sake of illustration and clarity.

DETAILED DESCRIPTION OF THE PRESENTLY PREFERRED EMBODIMENTS

It should be understood that the term "longitudinal," as used herein, means of or relating to length or the lengthwise direction, and in particular, the direction running between the front and back of the user. The term "laterally," as used herein means situated on, directed toward or running from side to side, and in particular, a direction running from the left to the right of a user. The terms "upper," "lower," "inner", and "outer" as used herein are intended to indicate the direction relative to the user wearing an absorbent garment over the crotch region, while the terms "inboard" and "outboard" refer to the directions relative to a centerline 8 of the garment and the absorbent composite 50. For example, the terms "inner" and "upper" refer to a "bodyside," which means the side closest to the body of the user, while the terms "outer" and "lower" refer to a "garment side".

The term "bodyside" should not be interpreted to mean in contact with the body of the user, but rather simply means the side that would face toward the body of the user, regardless of whether the absorbent garment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the absorbent garment is actually being worn by a user, regardless of whether any such outer garments are actually worn and regardless of whether there may be intervening layers between the component and any outer garment.

The phrases "removeably attached," "removeably attaching," "removeably connected," "removeably engaged," "releasably attached," "releasably connected," or "releasably engaged," and variations thereof, refers to two or more elements being connected or connectable such that the elements tend to remain connected absent a separation force applied to one, both or all of the elements, and where the elements are capable of being separated upon the application of a separation force. The required separation force is typically beyond that encountered while wearing the absorbent garment.

The phrases "fixedly secured," "fixedly engaged," "fixedly attached," "fixedly connected," and variations thereof, refers to two or more elements being connected or connectable such that they are not disconnected or otherwise separated, and are not intended to be separated or disconnected, during the normal operation and use of the absorbent garment.

The terms "connecting," "coupled," "attached," and "secured," and variations thereof, broadly covers two or more items being directly connected one to the other, or by way of one or more intervening members or components.

Figure 1:
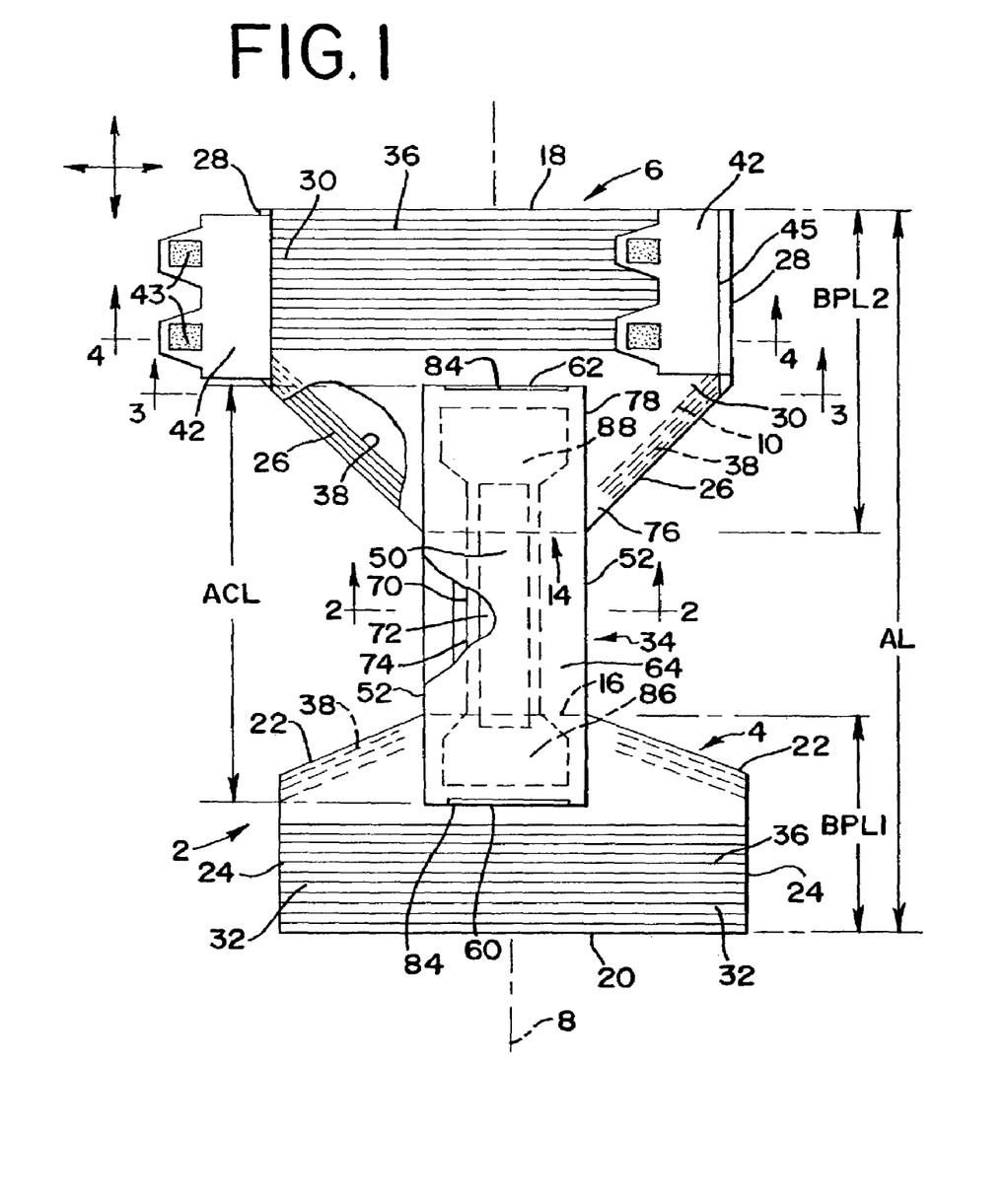
FIG. 1 is a plan view of a first embodiment of an absorbent garment taken from the bodyside thereof.
Figure 5:
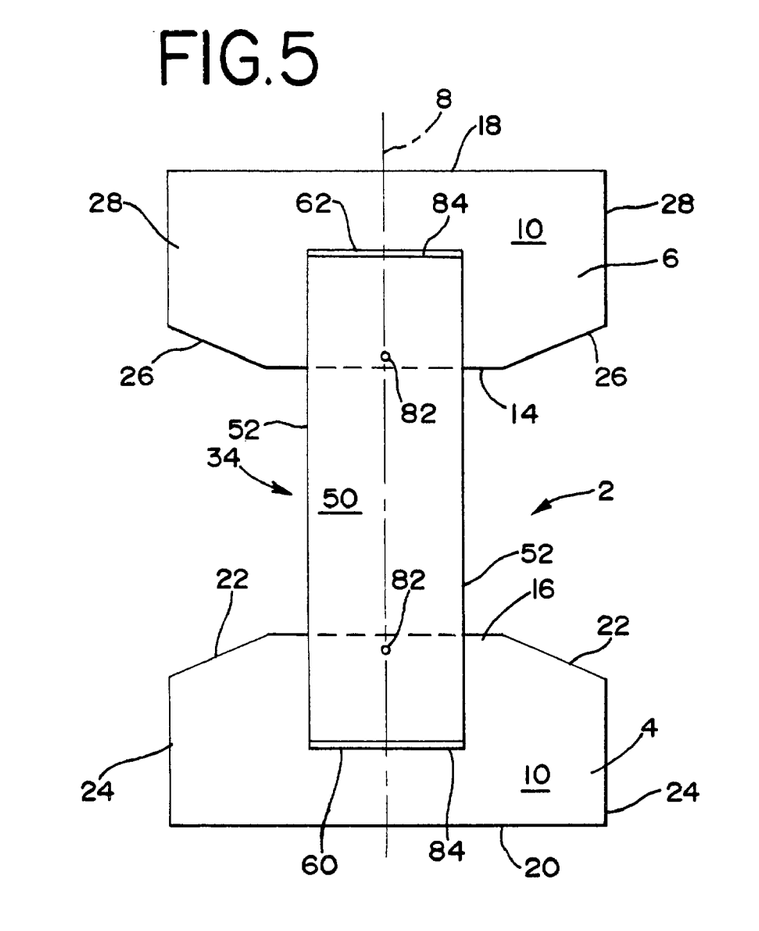
FIG. 5 is a plan view of a second embodiment of an absorbent garment taken from the bodyside thereof.
Figure 6:
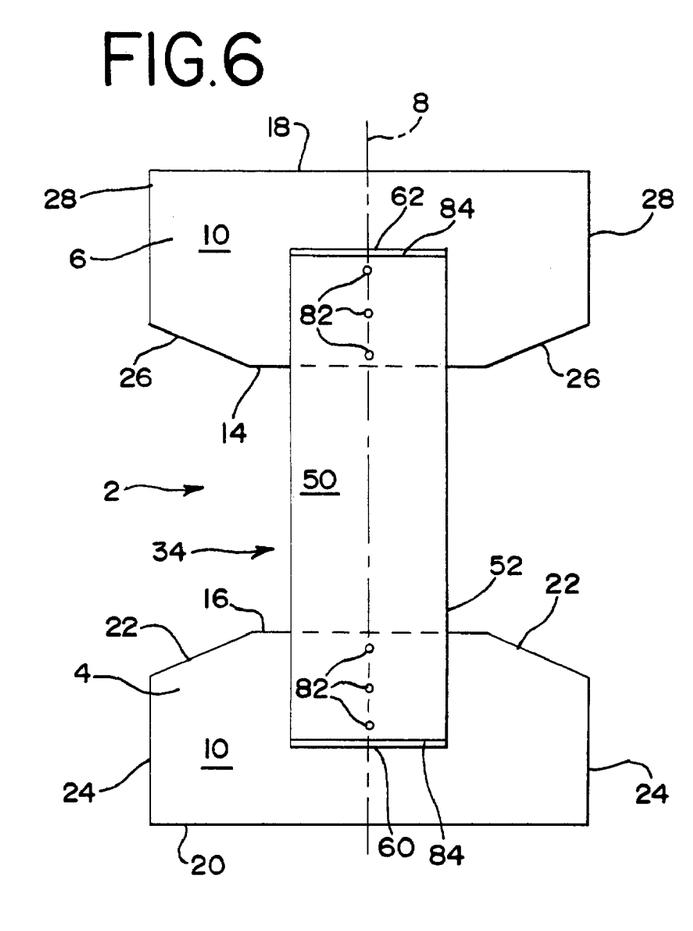
FIG. 6 is a plan view of a third embodiment of an absorbent garment taken from the bodyside thereof.
Figure 7:
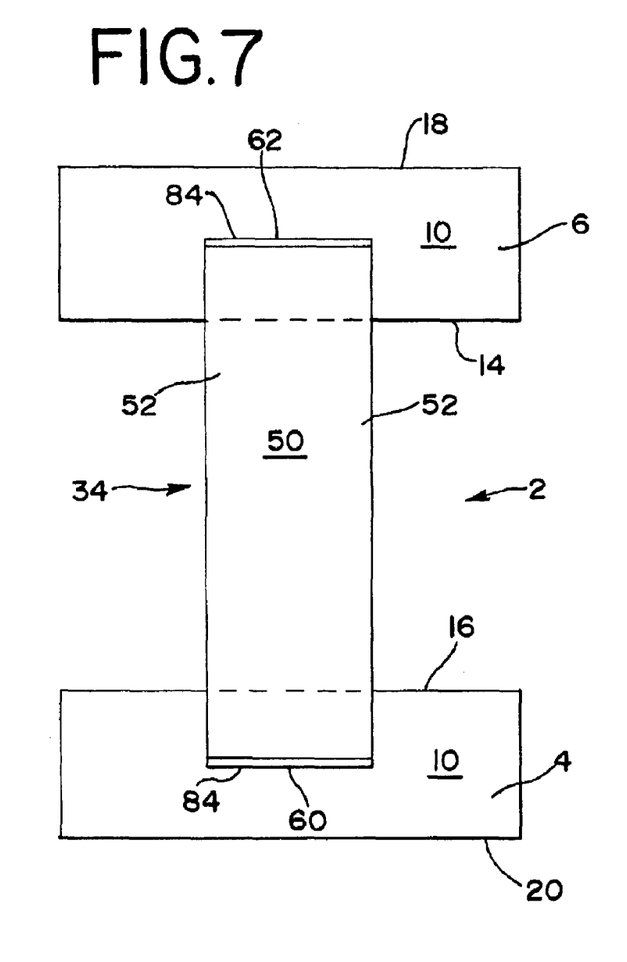
FIG. 7 is a plan view of a fourth embodiment of an absorbent garment taken from the bodyside thereof.
Figure 8:
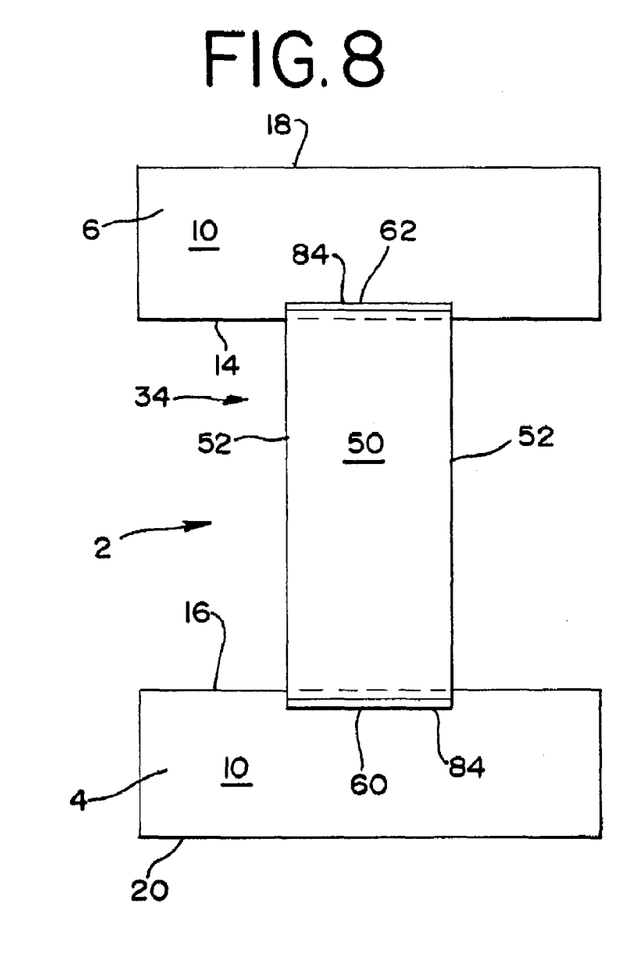
FIG. 8 is a plan view of a fifth embodiment of an absorbent garment taken from the bodyside thereof.
Figure 9:
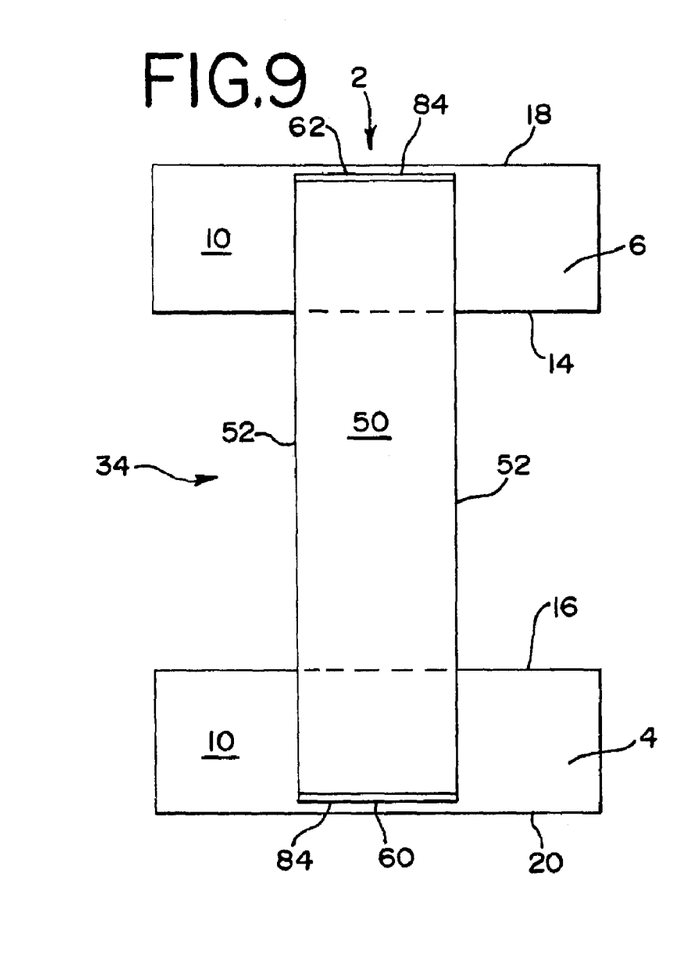
FIG. 9 is a plan view of a sixth embodiment of an absorbent garment taken from the bodyside thereof.

Referring to FIGS. 1 and 5-9, an absorbent garment 2 includes a first, front body panel 4 and a second, rear body panel 6. The term "body panel" refers to the portion(s) of the absorbent garment, whether made of one or more layers or substrates or of one or more pieces or components that is/are fitted circumferentially around at least the waist region of the user, including for example the user's lower back, buttock, hips and abdomen. The first and second body panels each have an inner, bodyside surface 10 an outer, garment side surface and a length, which is less the overall length of the absorbent garment. Each of the first and second body panels has a first and second longitudinally opposed terminal end edges 16, 14, 20, 18 forming waist and crotch edges respectively, and outer side edges. In the embodiment of FIGS. 1, 5 and 6, the side edges include including a tapered edge 22, 26 and an outboard edge 24, 28 formed along the outer periphery of laterally opposed ear portions 30, 32. Alternatively, as shown in FIGS. 7-9, the front and rear body panels do not include a tapered side edge, but rather the terminal crotch edge is substantially linear.

Referring to FIGS. 1 and 5-9, the first terminal edges 14, 16 of the first and second body panels are longitudinally spaced to form a gap or opening 34 therebetween in the crotch region of the garment, while the second terminal edges 20, 18 of the first and second body panels form front and back waist edges respectively. As shown in FIG. 1, a plurality, meaning two or more, of laterally extending elastic elements 36 can be secured to each of the first and second body panels. Likewise, one or more leg elastic elements 38 can be secured along the tapered side edge of the body panels to form a gasket with the leg of the user.

For example, as shown in FIGS. 1-4, each panel can be made of an elasticized composite panel material comprising two non-woven substrates 40 with the plurality of elastic strands 38, 36 sandwiched therebetween. The elastic strands are positioned in the waist regions and along the leg perimeters. A portion of the leg elastic elements 38 can extend under a side margin of an absorbent composite 50. The placement of the panel leg elastic elements further inward along the side edge provides for improved fit and performance of the garment. In one preferred embodiment, a plurality of elastic elements are spaced across substantially the entire waist portion of the front and rear body panel 4, 6, although they may be spaced across a lesser length. For example, elastic elements can extend along the upper waist portion and along the lower terminal edge defining in part a leg opening 34. In one embodiment, an elastomeric layer, such as a film, is disposed between the substrates to form the elasticized composite panel.

In one embodiment, the front body panel has a "non-elasticized" area wherein there are no elastic elements, or other elastic or electrometric backing members, incorporated therein or making up any portion of the thickness or cross-section of the body panel at that area. It should be understood, that in an alternative embodiment, one or more separate waist bands, with or without elastic elements, can be secured to one or both of the rear and front body panels, preferably along the upper terminal edges 20, 18 thereof. Likewise, one or more separate leg bands can be secured to one or both of the rear and front body panels along the leg open portions 22, 26 adjacent the leg openings 34. Alternatively, one or both of the body panels can be formed without any elastic elements.

The various waist and leg elastic elements can be formed from rubber or other elastomeric materials. One suitable material is a LYCRA® elastic material. For example, the various elastic elements can be formed of LYCRA® XA Spandex 540, 740 or 940 decitex T-127 or T-128 elastics available from E.I. duPont De Nemours and Company, having an office in Wilmington, Del.

In one embodiment, each body panel 4, 6 is formed as a composite, or laminate material, otherwise referred to as substrates or laminates, with the plurality of elastic strands sandwiched therebetween. For example, two or more layers may be bonded with various adhesives, such as hot melt, or by other techniques, including for example and without limitation ultrasonic bonding and heat pressure sealing. In one embodiment, the two layers are made of a non-woven material such as a spunbond material, a bonded carded material or other known materials. It should be understood that the body panels can be made of a single layer or substrate of non-woven material, or can be comprised of more than two layers or substrates. Of course, it should be understood that other knitted or woven fabrics, non-woven fabrics, elastomeric materials, polymer films, laminates and the like can be used to form one or more of the body panel layers. The term "non-woven" web or material, as used herein, means a web having a structure of individual fibers or filaments that are interlaid, but not in an identifiable manner and without the aid of textile weaving or knitting, as in a knitted or woven fabric.

In one embodiment, the body panel material can be secured to the elastic elements, such as strands or ribbons, which have been elongated and retracted, such that the material is gathered when the elastic elements are relaxed. Alternatively, the material can be gathered and laminated to non-elongated elastic elements. In one embodiment, the body panel includes a gathered elastic laminate made from nonwoven base sheets bonded with elongated elastic elements sandwiched therebetween.

In various embodiments, the body panel material may be substantially permeable to air or substantially impermeable to air. The body panel material also may be substantially liquid-permeable or substantially liquid-impermeable. In particular arrangements, the body panel material may be substantially nonelastomeric. In other aspects, the body panels can include an elastomeric material that is elastomerically stretchable at least along the lateral article width. Examples of such elastomeric composite materials can include a vertical filament laminate (VFL), neck-bonded-laminate (NBL), a stretch-bonded-laminate (SBL), a necked-stretch bonded laminate (NSBL) or a necked-thermal laminate, or the like, as well as combinations thereof. Exemplary NBL, SBL, and NSBL materials are described in U.S. Pat. Nos. 5,226,992, 4,981,747, 4,965,122, 5,336,545, 5,385,775, 5,414,470, 4,720,415, 4,789,699, 4,781,966, 4,657,802, 4,652,487, 4,655,760, 5,116,662 and 5,114,781, all of which are hereby incorporated herein by reference. Exemplary VFL materials are described in U.S. Provisional Patent Application Ser. No. 60/204,307, filed May 15, 2000 and entitled "Method and Apparatus for Producing Laminated Articles," and PCT application WO 01/88245 A2, both assigned to Kimberly-Clark Worldwide, Inc., the Assignee of the present application, with the entire disclosures of both being hereby incorporated herein by reference. Such laminates can provide an improved combination of cloth-like feel and elastomeric stretchability. The body panels can be composed of materials that are elastic or elastomeric and exhibit biaxial stretch characteristics or MD/CD stretch characteristics, or that are extensible composites. Additional waist and leg elastic elements can be added to, but are not necessarily required by, the body panels.

In one embodiment, the entirety of the body panels are elasticized, such that the entire body panel conforms to the body of the user without any spacing between the body panel and the user's body, and without the attendant bulkiness of a non-elasticized material.

In one embodiment, the body panels are breathable, cloth-like, multi-directional nonwoven laminates with stretch and/or extensible properties. In one embodiment, the non-woven layers are pre-necked, preferably between about 10% and about 80%, in the longitudinal direction, which provides extensibility in the longitudinal direction with minimum force.

The terms "extensible," "extensibility," and variations thereof as used herein means capable of being extended, and providing a selected elongation, for example between about 5% and about 70%, when subjected to an applied tensile force. The body panel also is preferably capable of providing a selected, sustained deformation when subjected to an applied tensile force and then allowed to relax for a selected time period beginning immediately after removal of the tensile force. Preferably the sustained deformation is a substantially permanent deformation. The selected elongation and sustained deformation preferably occur at least along the longitudinal direction of the garment, although it should be understood that it also could occur along the lateral direction, or both. Various extensible materials, and other acceptable materials that can be used for the body panels are described for example in U.S. Pat. No. 6,217,563, issued Apr. 17, 2001 to Kimberly-Clark Worldwide, Inc., the same Assignee as the present application, the entire disclosure of which is hereby incorporated herein by reference.

The extensibility of the non-woven material provides an increase in surface area without the retractive force of elastomeric materials. In one embodiment, body panel is extensible in at least the cross-direction, or longitudinal direction, with the material providing an elongation of at least about 1 cm when subjected to a tensile stress of 11.8 grams per cm. In addition, the body panel preferably provides a substantially permanent deformation of at least about 20% when it is subjected to a tensile stress of 19.70 grams per cm and is then allowed to relax under a zero applied stress for a period of 1 minute. Of course, it should be understood that the body panel can also be made extensible in the lateral direction.

In one embodiment, the front and rear body panels 4, 6 are made of non-woven laminates of two layers of longitudinally extensible 0.60 osy polypropylene spunbond material with elongated strands of Lycra® elastic sandwiched between the spunbond layers and thereafter adhesively bonded. In particular, the body panel material is necked in the cross direction. As used herein, the term "necked," and variations thereof, refers to any material that has been constricted in at least one dimension by applying a tensioning force in a direction that is perpendicular to the desired direction of neck-down. Processes that may be used to constrict a material in such a manner include, for example and without limitation, drawing processes. The elastics are then elongated in the machine direction and secured to the body panel material. The elastics are then allowed to retract so as to gather the necked spunbond material in the lateral (machine) direction thereby creating an elastically gathered non-woven body panel with longitudinal extensibility. The term "gather," and variations thereof, as used herein means puckered, or contracted into folds or wrinkles, which should be understood as including micro-pleats. In this way, the body panel can be elongated in both the longitudinal and lateral direction to conform to the body of the user when the garment is applied thereto. In particular, as the user pulls the garment up over their hips, the non-woven laminate body panels stretch in the lateral direction while the leg regions of the front and rear body panels conform to the crotch and body lines of the user. At the same time, the body panel material extends in the longitudinal direction to conform to the buttocks and stomach of the user. The extensibility of the body panels follows the natural curvature of user's body to provide conformance thereto. As the body panel extends in the longitudinal direction, the spacing between the laterally extending elastic elements 36, incorporated in one preferred embodiment, will increase.

In one embodiment, the body panel 4, 6 non-woven material is substantially hydrophobic, which may optionally be treated with a surfactant or otherwise processed to impart a desired level of wettability and hydrophilicity. In one particular embodiment of the invention, the body panel is a non-woven, wire-weave spunbond polypropylene fabric composed of about 1.6 denier fibers formed into a web having a basis weight of about 0.6 osy. One suitable non-woven material is the Corinth 0.60 osy, 1.6 dpf wireweave, nonwettable Metallocene (EXXON ACHIEVE 2854 PP) spunbond material manufactured by Kimberly-Clark Corporation, the assignee of the present application.

Referring to FIG. 1, the absorbent composite 50 connecting the front and rear body panels 4, 6 can be folded such that the side edges 24, 28 of the front and rear body panels 4, 6 are aligned wherein they can be fixedly secured at a seam. The seam can be formed by bonding, sewing or otherwise attaching the side edges. Alternatively, the product can remain "open," wherein the body panels are releasably secured with one or more fastening members as explained below.

In one embodiment the garment includes a combination of side edges that are secured to form a seam and fastening members that allow the fit of the absorbent garment to be adjusted. For example, fastening members can be attached to the front body panel and extend inboard relative to the outboard side edge of the front body panel from an attachment location, which is spaced inboard from the side edge. A landing member can be formed on or secured to the body panel to receive a refastenable portion of the fastening member. One or more lines of weakness can be provided along the front or rear body panel such that one or both of the body panels are breakable. The lines of weakness can comprise a perforation or other series of cuts, a thinning, breakage or separation of material, or a strip of a different kind of material bridging portions of the body panel that is more easily torn or broken than the other material thereof, which allow a user or the manufacturer to separate portions of the body panel. For example, the absorbent garment can be broken along the lines of weakness after the garment is applied to a user, or beforehand. In one embodiment, the fastening members are secured to the garment-side surface of the body panel.

It should be understood that, in other embodiments, as shown for example in FIG. 1, fastening members 42 are secured to the rear body panel 6 at attachment location 45 and engage the front body panel. Conversely, the fastener members can be secured to the front body panel and engage the rear body panel, for example along at least a portion that is not elasticized. In one embodiment, the fastening members are fixedly secured to the outer, garment-side surface of the front and/or rear body panels, and releasably engage the outer, garment-side surface of the front and/or rear body panels, although it should be understood that the fastening members could be fixedly secured to an inner body-side surface of front and/or rear body panels and releasably engage an inner, body-side surface of the front and/or rear body panels.

When incorporated into an absorbent garment, the fastening members 42 preferably include a refastenable portion 43, such as an array of hook members, adhesives, such as pressure sensitive adhesives, buttons, zippers, snaps and other releasable and reattachable fastening devices. In various preferred embodiments, the fastening member includes one, two or more than two tab members. In one embodiment, the fastening members comprise a carrier member, which is fixedly secured to the side portions of the front body panel with adhesive bonds, sonic bonds, thermal bonds, pinning, stitching or other known types of attachment. In alternative embodiments, the fastening members can be fixedly secured to the rear body panel or to one or both of the front and rear body panels, for example, at the seam, as explained above.

Figure 2:
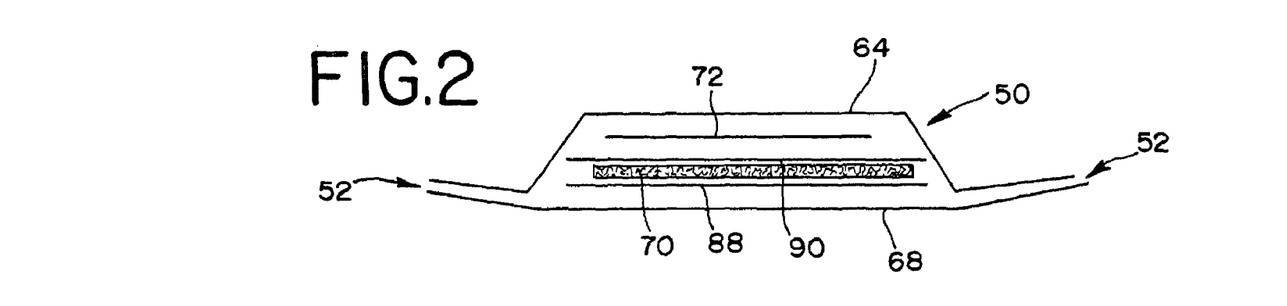
FIG. 2 is a schematic illustration of a cross-sectional view of the absorbent garment taken along line 2-2 in FIG. 1.

Referring to FIGS. 1 and 2, the absorbent garment includes an absorbent composite 50, otherwise referred to as a crotch member, having first and second opposed terminal end edges 60, 62. The terms "crotch member" and "absorbent composite" as used herein mean any material or assembly capable of absorbing liquids or bodily exudates, and may be formed from a single material or component, for example a retention portion, or a combination of materials and/or components.

In one embodiment, shown in FIGS. 1-4, the crotch member 50 includes a substantially liquid permeable topsheet 64, or liner, and a substantially liquid impermeable backsheet 68, or outer cover. A retention element 70 is disposed or sandwiched between the topsheet and the backsheet, which are connected. The topsheet, backsheet and other components of the crotch member 50 can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein. It should be understood that the term "retention element" refers to any material or assembly capable of absorbing liquids or bodily exudates, and may be comprised of a single material or component, or can be formed as a composite of several components.

Additional layers, including for example, a transfer layer 72, can also be incorporated into the crotch member 50. In one embodiment, the transfer layer does not run the entire length of the crotch member and is shorter than the retention element. The topsheet 64 can be indirectly joined to the backsheet 68 by affixing the topsheet to intermediate layers, such as the transfer layer 72 or retention portion 70, which in turn is affixed to the backsheet. The crotch member also may include barrier cuffs, or leakage control shields, formed along the opposite longitudinally extending edges thereof.

In one embodiment, the backsheet 68 is liquid impermeable, but may be liquid permeable, e.g., when an additional barrier layer is used with the retention portion. For example, in one embodiment, the backsheet can be made from a thin plastic film, or other flexible, substantially liquid-impermeable material. As used herein, the term "flexible" means a material that is compliant and which will readily conform to the general shape and contour of the body of the user. The backsheet prevents various bodily fluids and exudates from wetting or otherwise contaminating various bedding or outer garments worn by the user over the absorbent garment. In particular, the backsheet can include a film, such as a polyethylene film, having a thickness of from about 0.012 mm to about 0.051 mm.

In various constructions, the topsheet 64 can comprise various woven or nonwoven materials. For example, the topsheet can be composed of a meltblown or spunbonded web of desired fibers, and may also be a bonded-carded web. For example, the topsheet can be made of a substantially hydrophobic material, and the hydrophobic material may optionally be treated with a surfactant or otherwise processed to import a desired level of wettability and hydrophilicity. In one particular embodiment of the invention, the topsheet is a nonwoven,'spunbond polypropylene fabric composed of about 2.8-3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

In various constructions, the backsheet can comprise a woven or nonwoven fibrous web layer, which is treated or constructed, partially or wholly, to impart the desired levels of liquid impermeability to selected regions that are adjacent to or proximate the absorbent retention portion. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type has been employed to form the outercover of a HUGGIES® Ultratrim Disposable Diaper, which has been commercially available from Kimberly-Clark Corporation. The backsheet can provide the outercover of the article, particularly in the crotch region. Optionally, however, the article may include a separate outercover component member, as disclosed herein, which is additional to the backsheet. The outercover can be joined, for example, to one or more of the absorbent composite and/or body panels as explained above.

The backsheet may include a micro-porous, "breathable" material which permits gases, such as water vapor, to escape from the absorbent garment while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In various configurations of the invention, where a component, such as the backsheet is configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

In one preferred embodiment, the backsheet is sufficiently impermeable to liquid and semi-liquid materials to substantially prevent the undesired leakage of waste materials, defined as exudates, including for example urine and feces. For example, the backsheet member can desirably support a hydrohead of at least about 45 centimeters (cm) substantially without leakage. The backsheet member can alternatively support a hydrohead of at least about 55 cm, and optionally, can support a hydrohead of at least about 60 cm, or more, to provide improved benefits.

The backsheet and/or outercover also can be extensible. In one preferred embodiment, the backsheet and/or outercover is capable of providing an elongation of at least about 1 cm when subjected to a tensile force of 11.8 g/cm, and further provides a substantially permanent deformation of at least about 20% when subjected to a tensile force of 19.70 g/cm and is then allowed to relax under a zero applied stress for a period of 1 minute.

For example, the extensible member can be composed of a necked fiber, a creped fiber, a micro-pleated fiber, polymer films or the like, as well as combinations thereof. The fabrics may be woven or nonwoven materials, such as spunbond fabrics. One example of a suitable extensible material is a 60% necked, polypropylene spunbond having a basis weight of about 1.2 osy.

The backsheet and/or outercover also can be expandable, for example when it has one or more folds, e.g., one or more z-folds (not shown), or can be both extensible and expandable. The term expandable as used herein means to enlarge or to increase the extent or area, lateral and/or longitudinal, thereof, e.g., by unfolding one or more folds.

The retention element 70 is made of an absorbent material, which can be any material that tends to swell or expand as it absorbs exudates, including various liquids and/or fluids excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. Nos. 5,147,343 for Absorbent Products Containing Hydrogels With Ability To Swell Against Pressure, 5,601,542 for Absorbent Composite, and 5,651,862 for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

Figure 3:
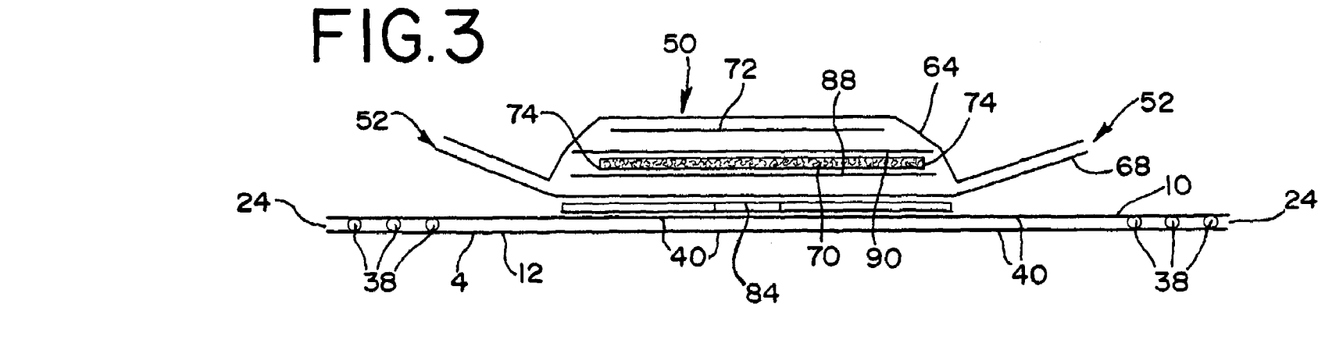
FIG. 3 is a schematic illustration of a cross-sectional view of the absorbent garment taken along line 3-3 in FIG. 1.
Figure 4:
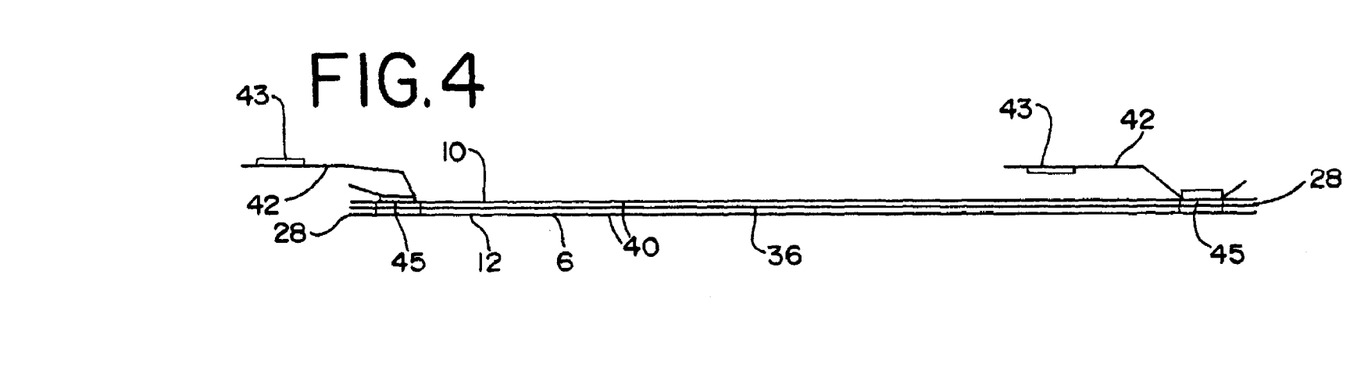
FIG. 4 is a schematic illustration of a cross-sectional view of the absorbent garment taken along line 4-4 in FIG. 1.

In various embodiments, the retention element 70 can be made of a single or dual layer of absorbent material. Alternatively, the retention portion can include a folded or multilayered configuration. The retention portion preferably has a length substantially equal to, or slightly shorter than, the length of the absorbent insert. As shown in FIGS. 2 and 3, the retention portion can include one or more barrier layers 88, 90 attached to the absorbent material 70. In one embodiment, an upper tissue substrate 90 is disposed adjacent the retention portion. In addition, a lower tissue substrate 88 can be disposed adjacent an opposite side of the retention element, or the tissue can completely envelope the retention element. The retention element, and the overall absorbent composite, can have a trapezoidal shape with first and second parallel terminal edges and non-parallel, linear side edges, wherein said first terminal edge is shorter than said second terminal edge.

As shown in FIGS. 1 and 5-9, the first terminal edge 60 overlies the front body panel 4 and the second terminal edge 62 overlies the rear body panel 6. Referring to the embodiment shown in FIG. 1, the opposite garment side of the end regions of the absorbent composite 50, and in particular, the outer, garment side surface of the backsheet, are secured to the bodyside surface of the first and second body panels 4, 6. Alternatively, the bodyside surface of the crotch member is secured to the garment side surface of the body panels. It should be understood that the absorbent composite 50 can be secured to the body panels using any of the methods of attachment described above, including for example various adhesives, stitching or other bonding methods.

The entire portion of the absorbent composite 50 overlapping the body panels 4, 6 can be attached thereto, or the crotch member can be minimally attached to the body panels, for example by one or more attachment locations 82 formed along the centerline 8 of the absorbent composite, or along an attachment location 84 at the terminal edges 60, 62 of the absorbent composite so as to allow the body panels to stretch from side to side and extend from front to back, or from the crotch to the waist.

For example, and referring to FIG. 1, the opposite garment side of the absorbent composite, and in particular, the outer, garment side surface of the backsheet 68, is secured to the bodyside surface 10 of the longitudinally spaced first and second body panels 4, 6. In the embodiment of FIGS. 1 and 7-8, the absorbent composite 50 is connected to the bodyside surface of the body panels 4, 6 only at the terminal edges 60, 62 thereof. Conversely, the body side surface of the top sheet of the absorbent composite can be secured to the garment side surface of the body panels. The attachment location 84 can extend laterally across the entire width of the absorbent composite at the terminal edge thereof, or across only a portion thereof, as shown for example in FIGS. 1 and 3. The term "location" means any region, dot or position, and is not limited to lines, whether continuous or intermittent.

It should be understood that the absorbent composite 50 can be secured using any of the methods of attachment described above. Moreover, it should be understood that the absorbent composite can be secured to the body panels with a continuous attachment line 84 along the terminal edges 60, 62, or a discontinuous attachment pattern, for example a plurality of laterally spaced apart attachment spots, or lines.

Referring to the embodiments of FIGS. 1, 5, 6 and 7, the terminal edges 60, 62 of the absorbent composite are secured to the body panels 4, 6 intermediate the terminal crotch and waist edges 16, 20, 14, 18 of the body panels. In the embodiment of FIG. 1, the terminal edges 60, 62 of the absorbent composite are longitudinally spaced from the terminal crotch edges 16, 14 of the front and rear body panels 4, 6 respectively, such that the absorbent composite has first and second unattached regions 86, 88 overlying the front and rear body panels respectively, with the "unattached regions" being defined as the portions of the absorbent composite that overlie the front and rear body panels but are not attached thereto.

Referring to the embodiment shown in FIG. 8, the terminal edges 60, 62 of the absorbent composite are secured to the body panels 4, 6 adjacent the terminal crotch edges 16, 14 of the body panels. Referring to the embodiment shown in FIG. 9, the terminal edges 60, 62 of the absorbent composite are secured to the body panels 4, 6 adjacent the terminal waist edges 20, 18 of the body panels 4, 6, respectively.

Referring to one embodiment of FIG. 1, the overall length of the absorbent garment, or article length (AL), is between about 23 inches and about 40 inches. Of course, the AL could be greater or less than lengths in that range. In various embodiments, the length of the absorbent composite (ACL) is between about 15% and about 95% of the AL, in other embodiments, the ACL is between about 25% and about 80% of the AL, and in other embodiments, the ACL is between about 50% and about 70% of the AL. In various embodiments, each body panel 4, 6 can have a length (BPL1 and BPL2 respectively) that is between about 20% and about 50% of the AL, in other embodiments, BPL1 and BPL2 are each between about 25% and about 45% of the AL, and in other embodiments, BPL1 and BPL2 are each between about 30% and about 40% of the AL.

Figure 10:
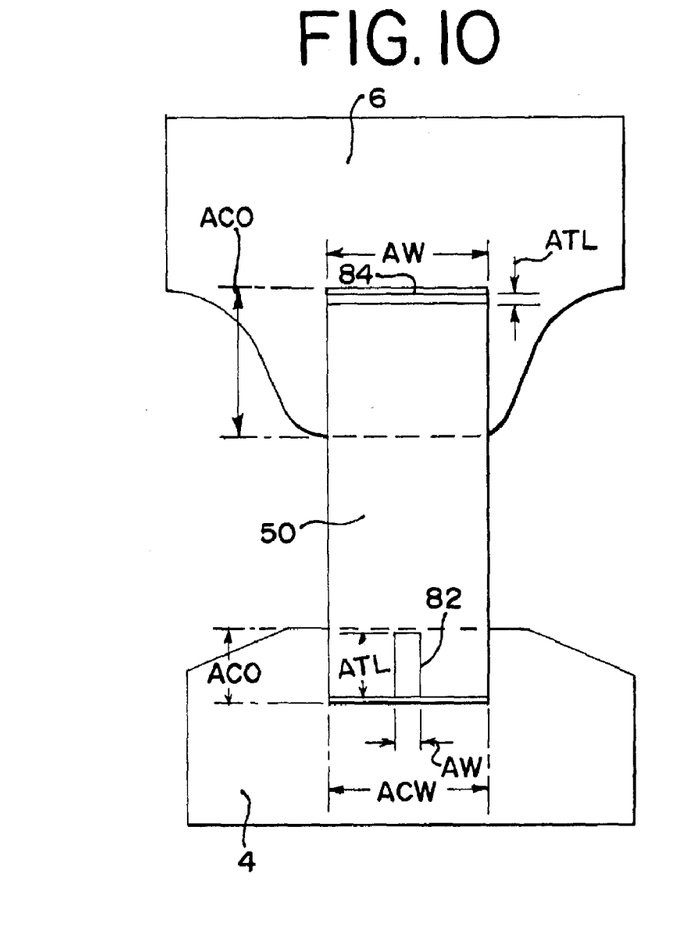
FIG. 10 is a plan view of a seventh embodiment of an absorbent garment taken from the bodyside thereof.

In all of the various embodiments, and with reference to FIG. 10, the longitudinal length (ATL) of the attachment location 84 at the terminal edges of the absorbent composite, or at any other location, is between about 2% and about 100% of the length of the overlap (ACO) of the absorbent composite 50 relative to the body panels, in other embodiments, the ATL is between about 2% and about 90% of the ACO, in other embodiments, the ATL is between about 3% and about 50% of the ACO, and in other embodiments, the ATL is between about 5% and about 20% of the ACO. It should be understood that the terminal edge 60 of the absorbent composite overlying the front body panel can be secured at any one of various attachment locations, e.g., the waist edge, the crotch edge or an intermediate position, while the terminal edge of the absorbent composite overlying the rear body panel can be secured to the rear body panel at any one of the same or different locations, e.g., the waist edge, the crotch edge or an intermediate position.

Referring to FIGS. 5 and 6, the absorbent composite 50 is further secured to the front and rear body panels 4, 6 at one or more attachment locations 82 longitudinally spaced from the terminal edges 60, 62 of the absorbent composite. For example, in FIG. 5, the absorbent composite 50 is secured to the front and rear body panels at an attachment location 82 located proximate the centerline 8 of the absorbent composite at a location spaced longitudinally from the terminal edges 60, 62, e.g., at a location adjacent the crotch edges 16, 14 of the body panels 4, 6, respectively. Alternatively, as shown in FIG. 6, the attachment location 82 proximate the centerline 8 is formed from a plurality of discrete, longitudinally spaced attachment points 82. In yet another embodiment, the attachment location extends continuously along the centerline from the terminal edges of the absorbent composite to the terminal crotch edge of the body panels. Other attachment locations and configurations are further disclosed in U.S. patent application Ser. No. 10/053,251, filed Nov. 2, 2001 and entitled "Absorbent Garment Having A Body Conforming Composite," which application is assigned to Kimberly-Clark Worldwide, the assignee of this application, and which application is hereby incorporated herein by reference.

In all of the various embodiments, and with reference to FIG. 10, the lateral width (AW) of the attachment locations 84, 82 of the absorbent composite is between about 2% and about 100% of the overall width (ACW) of the absorbent composite 50, in other embodiments, the AW is between about 2% and about 90% of the ACW, in other embodiments, the AW is between about 3% and about 50% of the ACW, and in other embodiments, the AW is between about 5% and about 20% of the ACW.

It should be understood that other ranges within the various enumerated ranges disclosed herein are contemplated, and further that suitable ranges are defined by the various lower and upper values specified in the various ranges, e.g., in one embodiment the ATL is between about 2% and about 20% of the ACO.

In operation, the user applies the garment 2, which, depending on the configuration thereof, includes pulling the garment on over the user's legs like underwear or fastening the garment around the user like a diaper. As the user applies and wears the garment 2, their legs apply a force to the opposite side edges 52 of the absorbent composite 50 in the crotch region thereof, and more specifically at the location or gap 34 between the body panels. The force of the user's legs tends to bunch or gather the absorbent composite 50 between the opposite side edges 52, thereby decreasing the overall width of the absorbent composite and improving the overall fit of the garment on the user. In particular, the attachment locations 84, 82 at the terminal edges 60, 62 of the absorbent composite, or along the centerline thereof, do not tend to restrict the gathering of the absorbent composite in the crotch region.

In another aspect, the manufacturer or retailer of such garments provides instructional information to the user, for example by way of textual or pictorial indicia on the packaging materials, about how the garment works. For example, the manufacturer or retailer can explain to the end user the advantages of the attachment locations, and the attendant ability of the absorbent composite to bunch or gather, as set forth herein, thereby improving the conformance and fit of the garment.

The present invention has been described with reference to preferred embodiments, those skilled in the art will recognize that changes may be made in form and detail without departing from the spirit and scope of the invention. As such, it is intended that the foregoing detailed description be regarded as illustrative rather than,limiting and that it is the appended claims, including all equivalents thereof, which are intended to define the scope of the invention.

The invention claimed is:

1. An absorbent garment comprising:
a front body panel comprising a terminal waist edge and a terminal crotch edge;
a rear body panel comprising a terminal waist edge and a terminal crotch edge, wherein said terminal crotch edge of said rear body panel is longitudinally spaced from and forms a gap with said terminal crotch edge of said front body panel; and
an absorbent composite comprising a top sheet, a back sheet, a retention element, first and second longitudinally spaced terminal edges and opposite laterally spaced side edges, wherein said retention element is disposed between said top sheet and said back sheet and comprises an absorbent material, wherein said absorbent composite bridges said gap between said front and rear body panels with said first and second terminal edges overlying and non-releasably connected to said front and rear body panels respectively and with at least a portion of said retention element overlying said front body panel, wherein said terminal edges of said absorbent composite are the only portion of said absorbent composite connected to said front and rear body panels, wherein said first and second terminal edges of said absorbent composite are directly connected to a bodyside surface of said front and rear body panels respectively.

2. The absorbent garment of claim 1 wherein said first terminal edge of said absorbent composite is longitudinally spaced from said terminal crotch edge of said front body panel, wherein said absorbent composite has a first unattached region overlying said front body panel.

3. The absorbent garment of claim 2 wherein said second terminal edge of said absorbent composite is longitudinally spaced from said terminal crotch edge of said rear body panel, wherein said absorbent composite has a second unattached region overlying said rear body panel.

4. The absorbent garment of claim 1 wherein said first terminal edge of said absorbent composite is connected to said front body panel at a position intermediate said terminal crotch and waist edges of said front body panel.

5. The absorbent garment of claim 1 wherein said first terminal edge of said absorbent composite is connected to said front body panel at a position adjacent said terminal waist edge of said front body panel.

6. The absorbent garment of claim 1 wherein said first terminal edge of said absorbent composite is connected to said front body panel at a position adjacent said terminal crotch edge of said front body panel.

7. The absorbent garment of claim 1 wherein said second terminal edge of said absorbent composite is connected to said rear body panel at a position intermediate said terminal crotch and waist edges of said rear body panel.

8. The absorbent garment of claim 1 wherein said second terminal edge of said absorbent composite is connected to said rear body panel at a position adjacent said terminal waist edge of said rear body panel.

9. The absorbent garment of claim 1 wherein said second terminal edge of said absorbent composite is connected to said rear body panel at a position adjacent said terminal crotch edge of said rear body panel.

10. The absorbent garment of claim 1 wherein said terminal edges of said absorbent composite are connected to said front and rear body panels at first and second attachment locations, wherein said absorbent composite overlaps each of said front and rear body panels along a first and second overlapping length respectively, and wherein said first and second attachment locations each have a longitudinal length of between about 2% and about 20% of said first and second overlapping lengths respectively.

11. The absorbent garment of claim 1 wherein said terminal edges of said absorbent composite are connected to non-elastic regions of said front and rear body panels.

12. A method of using an absorbent garment comprising:
providing said absorbent garment comprising a front body panel comprising a terminal waist edge and a terminal crotch edge; a rear body panel comprising a terminal waist edge and a terminal crotch edge, wherein said terminal crotch edge of said rear body panel is longitudinally spaced from and forms a gap with said terminal crotch edge of said front body panel; and an absorbent composite comprising a top sheet, a back sheet, a retention element, first and second longitudinally spaced terminal edges and opposite laterally spaced side edges, wherein said retention element is disposed between said top sheet and said back sheet and comprises an absorbent material, wherein said absorbent composite bridges said gap between said front and rear body panels with said first and second terminal edges overlying and non-releasably connected to a bodyside surface of each of said front and rear body panels respectively and with at least a portion of said retention element overlying said front body panel, wherein said terminal edges of said absorbent composite are the only portions of said absorbent composite connected to said front and rear body panels;
applying said absorbent garment to the body of a user having legs; and
applying a force to the opposite side edges of said absorbent composite with said legs of said user and thereby laterally gathering said absorbent composite between said opposite side edges thereof in at least the portion of said absorbent composite bridging said gap between said front and rear body panels.

13. The method of claim 12 wherein said first terminal edge of said absorbent composite is connected to said front body panel at a position intermediate said terminal crotch and waist edges of said front body panel.

14. The method of claim 12 wherein said first terminal edge of said absorbent composite is connected to said front body panel at a position adjacent said terminal waist edge of said front body panel.

15. The method of claim 12 wherein said first terminal edge of said absorbent composite is connected to said front body panel at a position adjacent said terminal crotch edge of said front body panel.

16. The method of claim 12 wherein said second terminal edge of said absorbent composite is connected to said rear body panel at a position intermediate said terminal crotch and waist edges of said rear body panel.

17. The method of claim 12 wherein said second terminal edge of said absorbent composite is connected to said rear body panel at a position adjacent said terminal waist edge of said rear body panel.

18. The method of claim 12 wherein said second terminal edge of said absorbent composite is connected to said rear body panel at a position adjacent said terminal crotch edge of said rear body panel.

19. The method of claim 12 wherein said terminal edges of said absorbent composite are connected to said front and rear body panels at first and second attachment locations, wherein said absorbent composite overlaps each of said front and rear body panels a first and second overlapping length respectively, and wherein said first and second attachment locations each have a longitudinal length of between about 2% and about 20% of said first and second overlapping lengths respectively.

20. A method of instructing a user on the use of an absorbent garment comprising:
providing said absorbent garment comprising a front body panel comprising a terminal waist edge and a terminal crotch edge; a rear body panel comprising a terminal waist edge and a terminal crotch edge, wherein said terminal crotch edge of said rear body panel is longitudinally spaced from and forms a gap with said terminal crotch edge of said front body panel; and an absorbent composite comprising a top sheet, a back sheet, a retention element, first and second longitudinally spaced terminal edges and opposite laterally spaced side edges, wherein said retention element is disposed between said top sheet and said back sheet and comprises an absorbent material, wherein said absorbent composite bridges said gap between said front and rear body panels with said first and second terminal edges overlying and non-releasably connected to a bodyside surface of each of said front and rear body panels respectively and with at least a portion of said retention element overlying said front body panel, wherein said terminal edges of said absorbent composite are the only portions of said absorbent composite connected to said front and rear body panels;

instructing the user to apply said absorbent garment to the body of the user.

21. The method of claim 20 further comprising instructing the user that wearing the absorbent garment will laterally gather said absorbent composite in the crotch region.

22. The absorbent garment of claim 1 wherein said first and second terminal edges are bonded to said front and rear body panels respectively.

23. The absorbent garment of claim 1 wherein said front and rear body panels each comprise a non-woven material.

* * * * *

UNITED STATES PATENT AND TRADEMARK OFFICE
CERTIFICATE OF CORRECTION

PATENT NO. : 7,591,810 B2  Page 1 of 1
APPLICATION NO. : 10/325456
DATED : September 22, 2009
INVENTOR(S) : Morman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1446 days.

Signed and Sealed this

Twenty-first Day of September, 2010

David J. Kappos
*Director of the United States Patent and Trademark Office*